United States Patent
Tran et al.

(10) Patent No.: US 8,608,697 B2
(45) Date of Patent: Dec. 17, 2013

(54) INSERTION INDICATOR FOR NEEDLE

(75) Inventors: Pelu Tran, Milpitas, CA (US); Khang Trong Dinh, San Jose, CA (US); Andrew Pipathsouk, Rockford, IL (US); Benjamin Chung, Los Altos, CA (US); Hongbin Li, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 186 days.

(21) Appl. No.: 13/041,284

(22) Filed: Mar. 4, 2011

(65) Prior Publication Data
US 2011/0218485 A1  Sep. 8, 2011

Related U.S. Application Data

(60) Provisional application No. 61/310,505, filed on Mar. 4, 2010.

(51) Int. Cl.
A61M 5/178 (2006.01)
A61M 1/00 (2006.01)
A61M 5/00 (2006.01)

(52) U.S. Cl.
USPC .. 604/117; 604/118; 604/164.12; 604/165.02

(58) Field of Classification Search
USPC .......... 604/107, 117, 164.02, 162.12, 165.01, 604/165.02, 167.01–168.01, 131, 26, 158, 604/118
See application file for complete search history.

(56) References Cited

U.S. PATENT DOCUMENTS

| | | | |
|---|---|---|---|
| 5,098,388 A | | 3/1992 | Kulkashi |
| 5,139,485 A | * | 8/1992 | Smith et al. ................... 604/158 |
| 5,295,969 A | * | 3/1994 | Fischell et al. ........... 604/168.01 |
| 5,324,268 A | | 6/1994 | Yoon |
| 5,334,150 A | | 8/1994 | Kaali |
| 5,352,206 A | | 10/1994 | Cushieri |
| 5,364,365 A | | 11/1994 | Wortrich |
| 5,374,252 A | | 12/1994 | Banks |
| 5,417,705 A | | 5/1995 | Haber |
| 5,423,770 A | | 6/1995 | Yoon |
| 5,562,696 A | | 10/1996 | Nobles |
| 5,685,820 A | | 11/1997 | Riek |
| 5,746,720 A | | 5/1998 | Stouder |
| 5,779,680 A | | 7/1998 | Yoon |
| 5,902,273 A | * | 5/1999 | Yang et al. ................... 604/118 |
| 5,938,640 A | * | 8/1999 | Maget et al. ................. 604/145 |
| 6,030,402 A | | 2/2000 | Thompson |

(Continued)

*Primary Examiner* — Bhisma Mehta
*Assistant Examiner* — Lauren M Peng
(74) *Attorney, Agent, or Firm* — Evans & Molinelli PLLC; Eugene J. Molinelli

(57) ABSTRACT

A method and apparatus are provided for a fluid level insertion indicator that provides immediate feedback to a surgeon by draining when a tip of a needle has entered a body lumen, such as peritoneal cavity. An apparatus includes a handle connected to a hollow needle and a hollow stylet that extends through the hollow needle and has a blunt distal end that includes an opening for passing fluid. A spring biases the stylet to extend past the sharp distal end of the needle absent resistance by tissue against the stylet. An at least partially translucent pressure chamber configured to hold a quantity of fluid under pressure is connected to the proximal end of the stylet. The pressure chamber and stylet form a conduit for passing fluid through the opening in the blunt distal end when the stylet extends past the sharp distal end of the hollow needle.

19 Claims, 9 Drawing Sheets

(56) References Cited

U.S. PATENT DOCUMENTS

| | | |
|---|---|---|
| 6,319,266 B1 | 11/2001 | Stellon |
| 6,884,253 B1 | 4/2005 | McFarlane |
| 6,905,489 B2 * | 6/2005 | Mantell et al. ................ 604/506 |
| 7,585,281 B2 | 9/2009 | Nezhat |
| 7,585,290 B2 | 9/2009 | Kathrani |

* cited by examiner

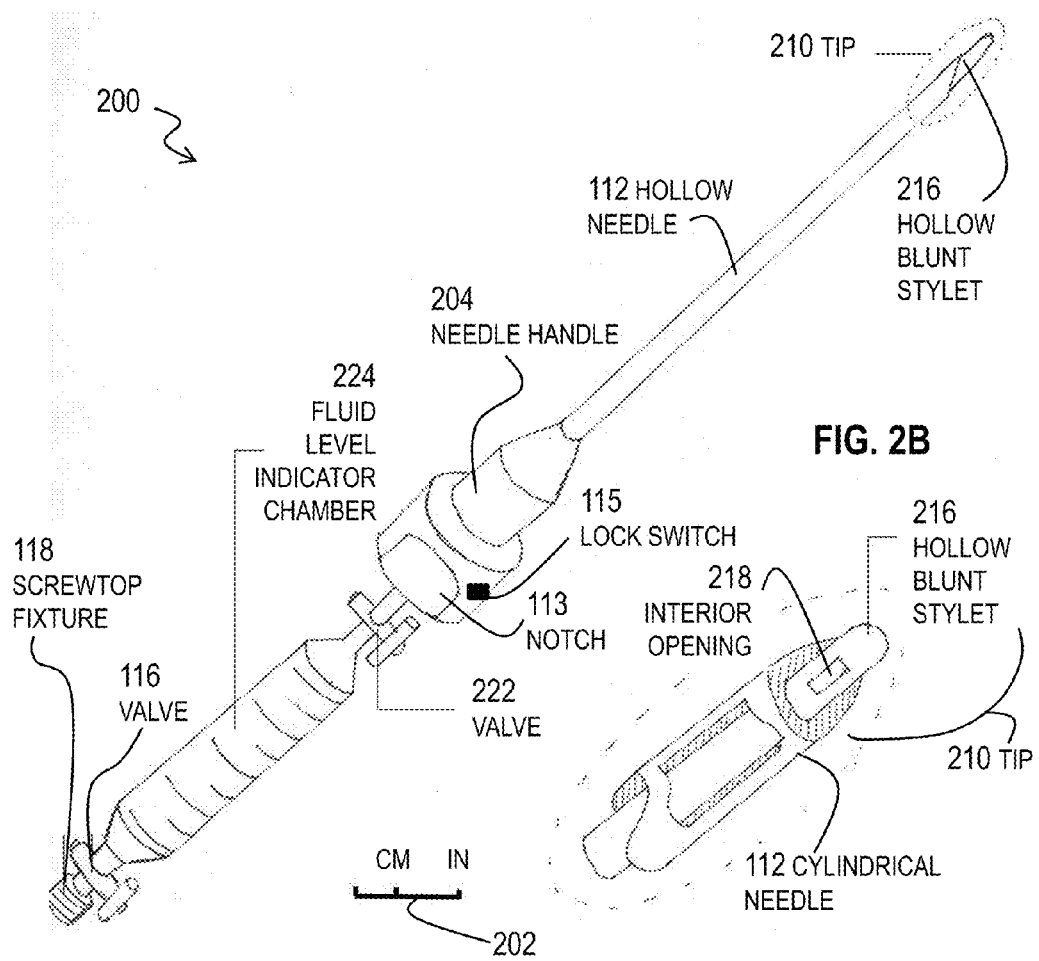

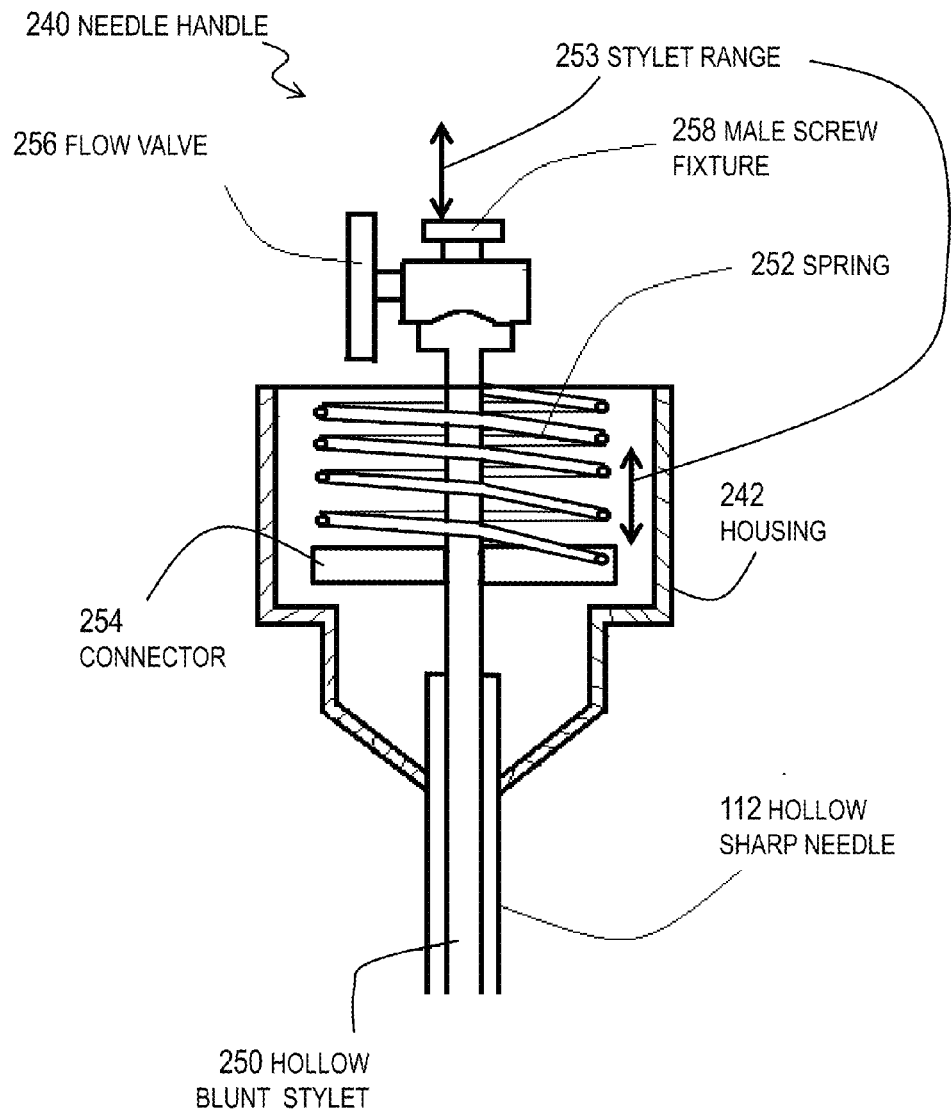

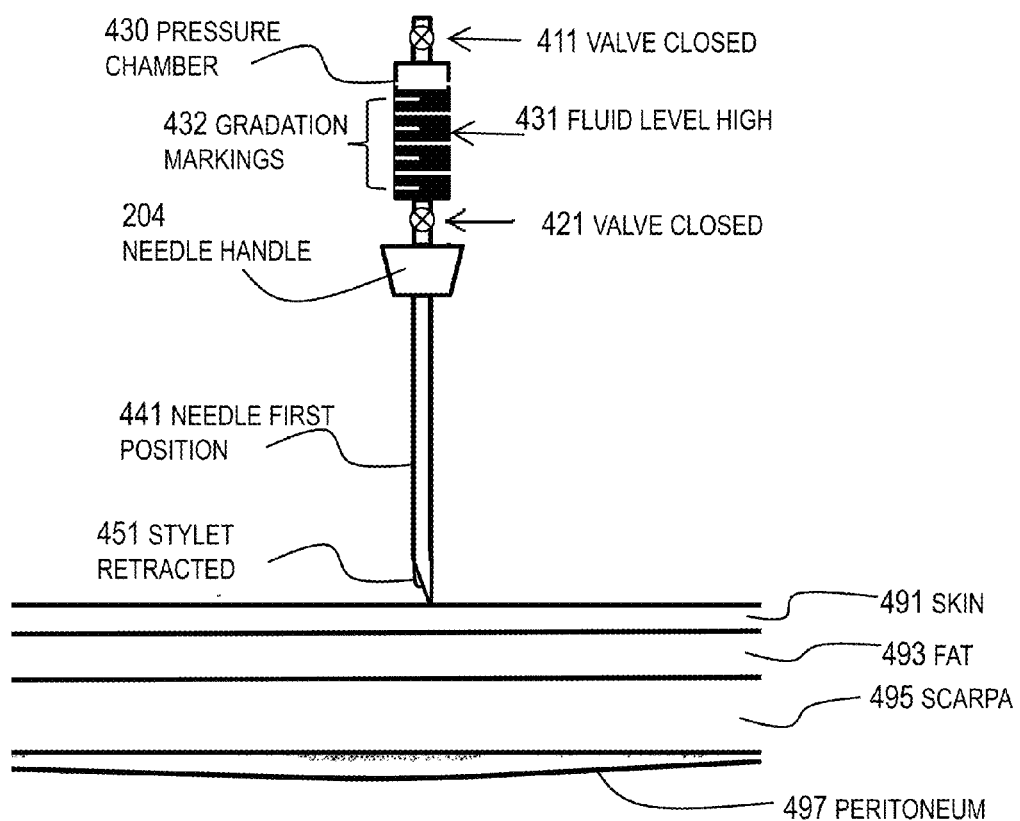

INSERTION INDICATOR FOR NEEDLE

CROSS-REFERENCE TO RELATED APPLICATIONS

This application claims benefit of Provisional Appln. 61/310,505, filed Mar. 4, 2010, the entire contents of which are hereby incorporated by reference as if fully set forth herein, under 35 U.S.C. §119(e).

BACKGROUND OF THE INVENTION

During all laparoscopic surgeries, a surgeon inserts a Veress needle into a peritoneum of a subject, such as a human patient; and, inflates the peritoneum with carbon dioxide ($CO_2$) to create room to operate. In a current approach, the Veress needle is blindly passed through an abdominal wall of a subject to provide a port of entry for $CO_2$ insufflation. There is only gross resistive feedback for Veress needle insertion.

This blind insertion can lead to problems, such as premature insufflation or puncturing of an organ inside the peritoneal sac. Furthermore, blind insertion leads to a high rate of first pass failure and results in some incidences of morbidity. For example, unsuccessful insertion of Veress needles, possibly leading to puncture of blood vessels or organs in the abdomen, can lead to significant injury. If not recognized during the operation (intra operatively) and repaired immediately, excessively penetrating Veress needles induce increased morbidity and mortality. At the other extreme, the needle may not be inserted far enough, and remain in tissue fascia, leading to embolism and potential tissue damage during insufflation. A 15% first pass failure rate, 0.3% morbidity rate, and 0.07% mortality rate are associated with use of the Veress needle, principally from either failing to fully penetrate into the peritoneum or puncturing vital organs and vessels.

Pressure sensor equipped Veress needles exist, but due to the variability of intraperitoneal and fascial pressure and differences between patients, they have not been widely accepted. Other existing approaches, such as a Lapcap, require a surgeon to retrain for a dramatically altered procedure called for by the device, or introduce significant drawbacks, such as needle slippage or additional tissue trauma, or some combination.

SUMMARY OF THE INVENTION

Applicants have determined that a need exists for a means to indicate immediately when a body lumen, such as the peritoneal sac, is penetrated, without one or more disadvantages of prior art approaches.

Techniques are provided for a fluid level insertion indicator that provides immediate feedback to a surgeon, indicating when a tip of a needle has entered a body lumen, such as the peritoneal cavity.

According to one set of embodiments, an apparatus includes a handle having a proximal end and a distal end connected at the distal end to a hollow needle having a sharp distal end for penetrating tissue. The handle and needle form a conduit for passing fluid or instruments or both through the distal end of the needle. The apparatus also includes a hollow stylet having a proximal end and a blunt distal end, which extends through the hollow needle. The proximal end of the stylet is disposed on a proximal side of the distal end of the handle and the blunt distal end includes an opening for passing fluid through the blunt distal end. A spring housed within the handle is configured to bias the stylet to extend past the sharp distal end of the needle absent resistance by tissue against the stylet. The apparatus also includes an at least partially translucent pressure chamber configured to hold a quantity of fluid under pressure. The pressure chamber has a distal end connected to the proximal end of the stylet. The pressure chamber and stylet form a conduit for passing fluid through the opening in the blunt distal end of the stylet when the stylet extends past the sharp distal end of the hollow needle.

According to another set of embodiments, a method includes puncturing a surface of skin of a subject with a sharp distal end of a hollow needle. A hollow stylet having a proximal end and a blunt distal end extends through the hollow needle and the blunt distal end includes an opening for passing fluid through the blunt distal end. An at least partially translucent pressure chamber holds a quantity of fluid under pressure and has a distal end connected through a closed flow valve to the proximal end of the stylet. The method further includes opening the flow valve after puncturing the surface of the skin of the subject. The method also includes, after opening the flow valve, advancing the distal end of the hollow needle through successive fascia of tissue in the subject while the fluid is observed to remain at a substantively constant level in the pressure chamber; and, stopping advance of the distal end of the hollow needle upon observing the fluid passing out of the pressure chamber.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2A is a block diagram that illustrates an example modified needle assembly, according to an embodiment;

FIG. 2B is a block diagram that illustrates a detail of an example tip of the modified needle assembly, according to an embodiment;

FIG. 2E is a block diagram that illustrates an example needle handle assembly, according to an embodiment;

FIGS. 4A-4C are block diagrams that illustrate operation of an example modified needle assembly using the method of FIG. 3, according to an embodiment.

DETAILED DESCRIPTION

Figure 1:
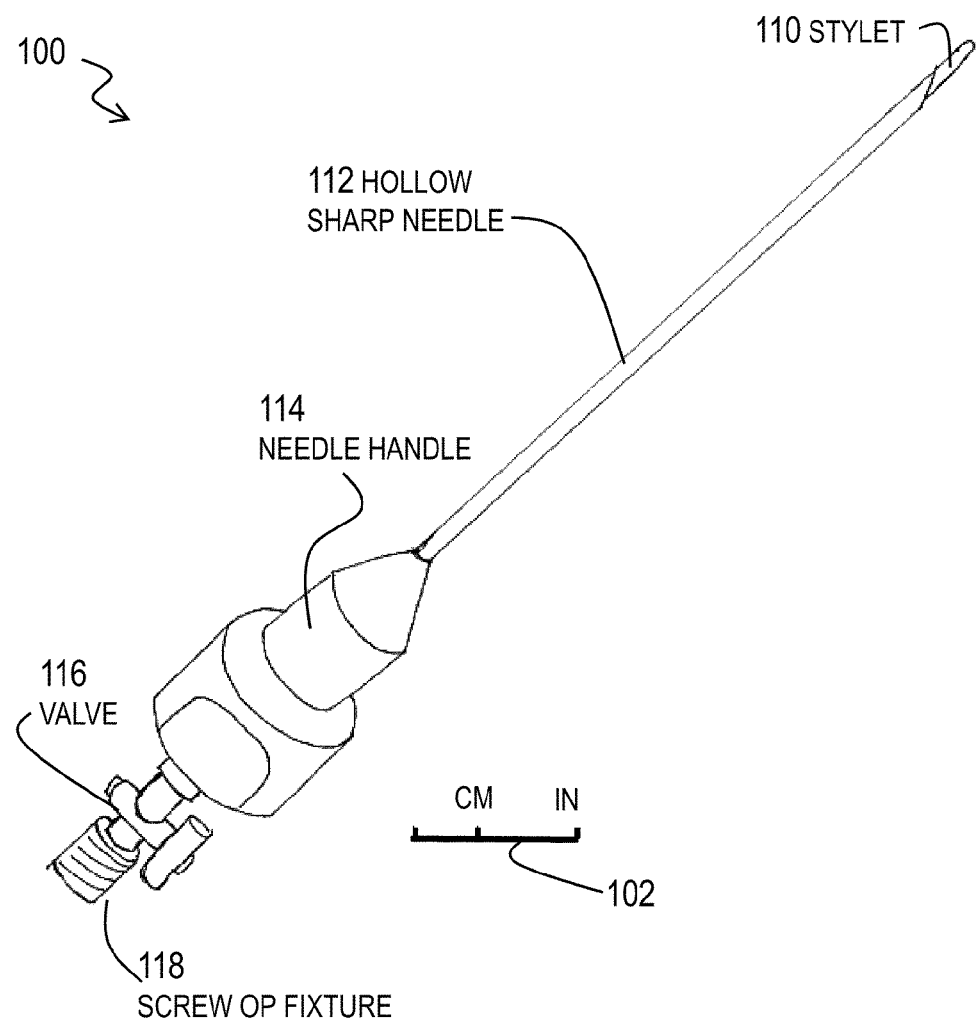
FIG. 1 is a block diagram of an example Veress needle assembly.

A method and apparatus are described for indicating complete insertion in a body lumen. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of insufflation of a peritoneal cavity for abdominal laparoscopic surgery. However, the invention is not limited to this context. Other embodiments are used for determining insertion into a body lumen elsewhere in a subject, such as a colon, a bladder, a lung, or a blood vessel, for any purposes, including for purposes other than insufflation or laparoscopic surgery. For example, in some embodiments, the needle assembly is used for insertions into a central line or other depth-sensitive blind insertions.

Many situations in surgical intervention require entry into a body cavity or lumen of a tissue within the body. While this initial step may not be directly part of an intervention or therapy itself, it can provide a portal through which to deliver intervention or therapy. The advantage of operating within already available spaces within the body is attractive because collateral damage to the patient can be minimized. As such, it is often desirable to minimize the damage done by the initial entry. In this context, body cavities or lumens are most often accessed not by scalpels but via needles (often of the Veress type).

While the subsequent surgeries are highly technical and precise, the initial penetration into a body cavity or lumen is often done without visual feedback and often depends upon the manual reflex of the physician. In essence, the act of puncturing the body with a needle is blind. There are two major consequences to this limitation. Firstly, the blind nature of the initial pass into the body creates a precarious situation in which there is a real possibility of unintentional damage to vital organs or vessels. Secondly, the inability to identify where the sharp end of the needle is, dramatically increases the rate of failure to properly reach the intended space or target. For many minimally invasive procedures that are otherwise straightforward, the step of blindly passing a needle into the body is often the one which causes the most anxiety. Furthermore, failing to reach the intended space or target on the first pass is itself a cause for secondary morbidity and mortality. Failure during the blind pass procedure is mostly due to incomplete penetration into the peritoneum using a Veress needle. Importantly, there are also incidences of morbidity associated with this single maneuver. It has been reported that as many as 0.9 in 1000 patients suffer major organ damage, 0.4 in 1000 suffer bowel injury, and 0.3 in 1000 suffer vascular injury due to the blind insertion of a typical Veress needle. Moreover, there is a significant increase in physician anxiety with each subsequent attempt, which has been associated with increased morbidity. These rates, while relatively low compared to other major surgeries, are significant given that more than a million laparoscopic surgeries are performed annually.

There have been numerous attempts in publication to redress the blind nature of initial needle passage into a body cavity or lumen. Most iterations focus on providing physicians with some sort of sensory feedback that informs on the location of the sharp end of the needle. Some authors have attempted to place fiber optic cameras at the sharp end to provide real time, visual feedback. Unfortunately, miniaturizing this technology to a scale where it does no more damage than common needles has been exceedingly daunting. Others have attempted to place piezoelectric pressure sensors at the tip to indicate the putative drop in gauge pressure upon entry into a body cavity or lumen. Unfortunately, there is enormous variability in the change in pressures between patients, the information is often equivocal, and the pressure sampling suffers from significant lag. In the context of the average pass lasting less than 20 seconds, this approach remains substantively irrelevant.

In some applications, mechanical control is a substitute or supplement to sensory feedback. Veress-type needles include a retractable blunt stylus that is placed within the hollow interior of the needle. The blunt tip retracts when puncturing through tissue but deploys beyond the sharp tip when there is no resistance from tissue, as in a body lumen. Some approaches include a mechanical lock which prevents the blunt tip from retracting, once extended. This feature putatively enables the physician to control when the needle is actually capable of puncturing tissue. However, even with this feature, the procedure remains inherently blind; it still depends upon the physician to determine when the needle has reached the appropriate space or target.

In laparoscopic surgery, specifically, where entry into an abdominal space is desired, a suction cap is proposed as a means of mechanical control. The proposed apparatus uses suction to lift up a portion of the abdominal wall such that there is more space between the peritoneum and vital organs. However, in many cases, the viscera are adhered to the abdominal wall and suction does little to prevent inadvertent injury. Moreover, this procedure requires removal and replacement of the needle after the initial pass, which in effect requires a second pass of the needle.

1. Overview

A modified needle assembly includes a fluid level gauge that signals when the surgeon has properly penetrated a body lumen, e.g., for insufflations for laparoscopic surgery, by draining fluid from the indictor into the lumen of the body.

In some embodiments, the safety and reliability of peritoneal insufflation for laparoscopic surgery is improved. In one example embodiment, a clear fluid chamber about 6 centimeters (cm, 1 cm=$10^{-2}$ meters) high, and on the order of one centimeter in diameter is attached via a fluid flow valve to a Veress type pneumo-needle. The chamber is filled with about 8 milliliters (ml, 1 ml=$10^{-3}$ liters) of a saline-based indicator solution which may be pressurized up to about 20 millimeters of Mercury (mm Hg, 1 mm=$10^{-3}$ meters) above atmospheric pressure—e.g., a pressure of about 1.03 atmospheres. In various other embodiments, a different amount of fluid and volume or cross section of the fluid chamber or pressure is used, or some combination. The amounts are selected to be large enough to be noticed by a surgeon, e.g., about 5 ml, up to a largest amount that does not render the needle unwieldy, e.g., up to about 100 ml. Another end of the chamber serves as an inlet for a gas, e.g., for pressurized $CO_2$ insufflation of the peritoneal cavity. In various other embodiments, the other end of the chamber includes a flow valve or is open to the atmosphere. Some embodiments do not allow the fluid chamber to be pressurized, until a pressurized supply of gas is attached to the open end. In some such embodiments, a means is included at the open end for attaching an insufflation gas supply; for example, the open end is threaded to accept a pressure fixture on or connected to an insufflation gas supply.

2. Example Embodiments

FIG. 1 is a block diagram of a Veress needle assembly 100, commonly used during insufflation for laparoscopic surgery. A scale 102 indicates an approximate size for various components. The Veress needle assembly 100 includes a hollow needle 112, such as a metal cylindrical tube, with blunt stylet (small stylus) 110 extending from inside the needle 112 at a distal end away from a surgeon. A needle handle 114 at a proximal end includes a spring housing and remains outside the subject during use. A valve 116 and screwtop fixture 118 are configured for connecting to a pressurized source of insufflation gas, such as pressurized $CO_2$, and allowing or stopping pressure communication with an inside of the hollow needle 112. Within a body lumen, the blunt stylet 110 is extended past the needle to reduce the chances of perforating an organ inside the peritoneal cavity. The stylet is hollow with an opening at the extended part to allow insufflation with $CO_2$ gas through the stylet.

FIG. 2A is a block diagram of a modified needle assembly 200, according to an embodiment. A scale 202 indicates an approximate size for various components. The modified needle assembly 200 includes the hollow needle 112, valve 116 and screwtop fixture 118, described above. The handle 204 is often modified from the handle 114 of the standard needle assembly. Thus, the assembly 200 includes a handle 204 having proximal end and distal end connected at the distal end to a hollow needle 112 having a sharp distal end for penetrating tissue, wherein the handle and needle form a conduit for passing fluid or instruments or both through the distal end of the needle.

The modified needle assembly 200 includes a modified hollow blunt stylet 216, as described below with reference to FIG. 2B. FIG. 2B is a block diagram of a detail of a tip 210 of the modified needle, according to an embodiment. In this embodiment, the distal tip 210 of the needle assembly 200 includes the distal end of the hollow blunt stylet 216. The stylet 216 has an opening 218 at its blunt, distal end that allows fluid flow out of its hollow interior. The opening 218 is configured and oriented in such as way as to prevent lodging of tissue which would prevent flow out of the opening 218 when extended past the sharp distal end of the needle 112. Thus, the blunt distal end includes an opening for passing fluid through the blunt distal end of the stylet 216. The blunt stylet 216 is extended to reduce the chances of perforating an organ inside the peritoneal cavity. The interior opening 218 allows the fluid in indicator chamber 224 to drain through the hollow stylet 216 into the body lumen, such as the peritoneal cavity, when valve 222, if present, is open.

In addition, as illustrated in FIG. 2A, the modified needle assembly 200 includes a fluid level indicator pressure chamber 224 and valve 222 to provide stoppable fluid communication with an inside of hollow stylet 216. The chamber 224 has at least partially translucent or fully transparent walls to make visible any liquid inside the chamber 224. Thus, the apparatus includes an at least partially translucent pressure chamber 224 configured to hold a quantity of fluid under pressure. Because the liquid itself is visible, a float used in some indicators is not included in the pressure chamber 224. In some embodiments, the chamber 224 is made of a single transparent material and is entirely transparent. Thus, in some embodiments, the pressure chamber 224 is at least partially transparent.

The pressure chamber 224 has a distal end connected to the proximal end of the stylet 216 (e.g., at valve 222). As a result, the pressure chamber and stylet form a conduit for passing fluid through the opening 218 in the blunt distal end of the stylet 216 when the stylet 216 extends past the sharp distal end of the hollow needle 112. In embodiments with valve 222, the assembly 200 includes a flow valve 222 disposed where the pressure chamber 224 is connected to the stylet 216.

In some embodiments, the walls include one or more markings that indicate volumes of different portions of the chamber 224. These markings can be used by an operator, such as a surgeon, to determine how much fluid is initially in the chamber and how much fluid, if any, has drained through the hollow stylet into the body lumen. Thus, in some embodiments, the pressure chamber 224 further comprises gradation markings; and the colored fluid is a different color from a color of the gradation markings.

The assembly 200 includes a retractable blunt stylet 216 that is biased to a position beyond the sharp, distal tip of a needle in which it runs internally and concentrically. The length and diameters of the stylus and needle vary in various embodiments, depending on the desired rate of fluid or instrument delivery via the portal created by the device.

Both the needle and the stylet are attached to a handle or housing 114 of a shape and dimension which accommodates a spring apparatus, as depicted in FIG. 2E described in more detail below, that biases the stylet to the deployed position. Thus, a spring is housed within the handle 114 for biasing the stylet 216 to extend past the sharp distal end of the needle 112 absent resistance by tissue against the stylet. The housing may have a notched portion 115 which allows for easy handling with simply the thumb and index finger.

Thus the apparatus includes a hollow stylet 216 having a proximal end and a blunt distal end, which extends through the hollow needle 112. The proximal end (e.g., at valve 222) of the stylet is disposed on a proximal side of the distal end of the handle 204; and the blunt distal end includes an opening 218 for passing fluid through the blunt distal end.

In the illustrated embodiment, the needle handle 204 includes a lock switch 115 that moves a cantilever into place, preventing the blunt tip from retracting. In other embodiments, other locking mechanisms are used, such as the latching mechanism described in U.S. Pat. No. 5,374,252, which locks the blunt tip "protector" into place after the penetration has been achieved; or the mechanism of U.S. Pat. No. 5,364,365, which uses a piercing obturator that can be locked either automatically or manually by the surgeon via a reciprocal rod located at the handle, the contents of each of which are hereby incorporated by reference as if fully set forth herein, except for the terminology is inconsistent with that used herein.

Figure 2C:
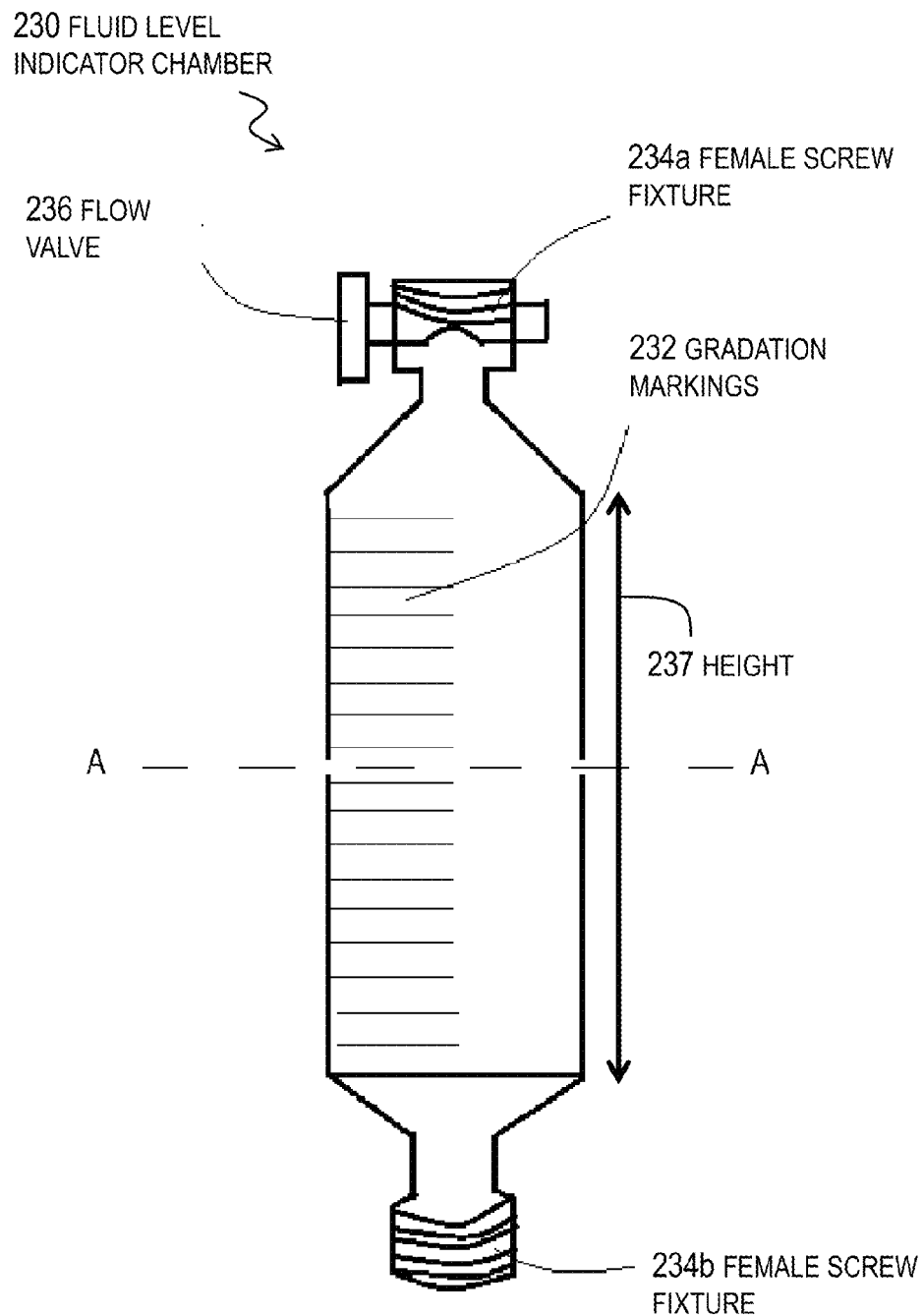
FIG. 2C is a block diagram that illustrates a detail of an example fluid level indicator chamber, according to an embodiment.

FIG. 2C is a block diagram that illustrates a detail of an example fluid level indicator pressure chamber 230, according to an embodiment. Chamber 230 is a particular embodiment of a pressure chamber, such as a particular embodiment of chamber 224. In this embodiment, the chamber 230 is completely modular. After the successful passage of the needle into the desired space of a body lumen, the indicator can be removed via the female screwtop fixture 234b. The chamber 230 itself is clear, e.g., either translucent or transparent, at least in part, allowing the visualization of a medical grade dye. Gradation markings 232 of a color with noticable contrast to the dye are disposed on the sides of the chamber to allow for referencing. These markings also allow for quantification of dye flow rate, should that be desired (i.e. for teaching purposes). The chamber 230 is pre-pressurized to a gauge pressure above zero (one atmosphere), allowing the indicator fluid to evacuate more rapidly, even when the chamber 230 is not above the distal end of the stylet 216. However, the pressure should not be so high as to induce leeching through fascia or other tissue. A pressure of about 1.02 to about 1.5 atmospheres (gauge pressures from 0.02 to 0.5 atmospheres) is useful. A proximal female screwtop fixture 234a with a flow valve allows the contents of the chamber to be renewed and the loading pressure to be modified by removeably connecting to a pressure source (e.g., a pump or pressurized $CO_2$ supply). Thus, the pressure chamber 230 includes a first fixture 234a on its proximal end for connection to a source of pressure. In some embodiments, the pressure chamber includes a flow valve 236 disposed at its proximal end, wherein the flow valve is configured for retaining pressure in the pressure chamber 230 after removal of the source of pressure.

Figure 2D:
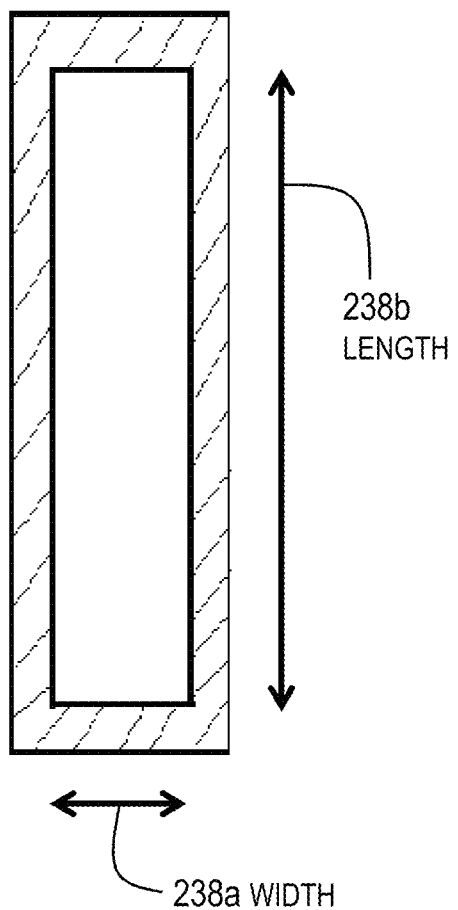
FIG. 2D is a block diagram that illustrates an example cross section of the chamber of FIG. 2C, according to an embodiment.

FIG. 2D is a block diagram that illustrates an example cross section of the chamber of FIG. 2C, according to an embodiment. The chamber has a cross section of small cross sectional area. This characteristic can be achieved via a rectangular cross section as shown or any shape with a relatively large eccentricity. The small cross sectional area of the chamber allows for rapid evacuation of the visualization agent. This is advantageous given the short time scale of the procedure, in which irreversible damage to vital organs and vessels may occur in less than a second.

The long dimension, length 238b, provides for good visibility even in the peripheral vision of a physician operating the device. The short dimension, width 238a, provides for a small cross sectional area and rapid draining of the fluid upon flow communication with the body lumen. Although drawn as a rectangle, in other embodiments other cross sectional shapes are used, such as oval shaped chambers. Thus, the pressure chamber 230 has a cross sectional length 238b large enough to be easily viewed by a person operating the apparatus and a cross sectional width 238a small enough so that passing a small volume of fluid through the stylet opening 218 makes a noticeable change in a fluid level in the pressure chamber. For example a cross sectional shape with an eccentricity from about 5 to about 8 is useful for visibility and quick draining. That is, the ratio of the major to minor axis of a rectangle or ellipse should be in the range from about 5 to about 8. This would mean that a rectangular cross section is about 1 cm by about 2 mm in some embodiments. The higher the eccentricity, the smaller the cross-sectional area. An advantage of a rectangular cross section is the simplicity of manufacture.

FIG. 2E is a block diagram that illustrates an example needle handle assembly 240, according to an embodiment. The handle assembly 240 is a particular embodiment of needle handle assembly 204 and includes hollow blunt stylet 250 that is a particular embodiment of the stylet 216, both depicted in FIG. 2A. The handle assembly 240 includes housing 242, hollow sharp needle 112, spring 252 and hollow blunt stylet 250 with connector 254. The blunt stylet 250 is mechanically coupled to at least one spring, e.g., spring 252, which biases the stylet 250 to the deployed position extended beyond the sharp tip of the needle 112 (as shown in FIG. 2B). For example, the hollow stylet 250 is connected to spring 242 by connector 254. The change in position of the stylet relative to the housing 242 from the deployed position to the retracted positions is illustrated by the stylet movement range 253. In other embodiments, other mechanism are used, such as rubber or metal bands, to provide the desired bias toward the deployed position of the stylet 216.

In various embodiments, the hollow interior of the needle 112 terminates upon interfacing with the housing 242 or continues into the housing in such a way that it does not disrupt the travel of the blunt stylet 250.

The hollow interior of the stylet 250 is continuous with a proximal flow valve 256 that controls whether or not the indicator dye or any attached fluid or gas source can flow. Thus, a flow valve 256 is disposed where the pressure chamber is connected to the stylet. The male screwtop fixture 258 is one example of a fixture used to attach the fluid level indicator pressure chamber 230 or fluid source or insufflation gas source. Thus the stylet 250 includes a first fixture 258 on its proximal end and the pressure chamber 230 includes a complementary second fixture 234b on its distal end and the pressure chamber 230 is removeably connected to the stylet 250 through the first and second fixtures.

Although particular components are depicted in the illustrated embodiments, in other embodiments, one or more components may be omitted or replaced with similarly functioning components. For example, in some embodiments, valve 222 is omitted and the interior of chamber 224 is in continual fluid communication with the hollow interior of blunt stylet 216. In some embodiments, the manually operated valve 222 is omitted or replaced with an automatic valve that opens when pressure from tissue being penetrated by the needle forces the blunt stylet to recede further into the needle to a retracted position, or when the spring moves the stylet past the sharp distal end of the needle. In some embodiments, the chamber 224 is permanently fixed to the stylet 216; and, in some embodiments, the chamber is removeably connected to the stylet with complementary fixtures other than male and female screw fixtures, such as clamp and gasket fittings, or bolted flanges.

This assembly 200 can be produced at scale without any specialized manufacturing techniques. It is desirable that the assembly 200 is manufactured in sterile conditions or sterilized before packaging. But because it is disposable, in some embodiments, many of the elements do not necessarily have to be specified to withstand temperature or pressure sterilization, or some combination. Some parts which comprise both the standard and modified needle assemblies are readily available in large volume (e.g., greater than 100,000 pieces).

In some embodiments, certain plastic components (e.g., valves, chambers, and spring housing) are manufactured using plastic injection molding of various materials, e.g., poly-ethylene, poly-carbonate, and acrylonitrile butadiene styrene (ABS), respectively. As indicated above, at least a portion of the walls of the chamber 224 are at least translucent to indicate the amount of fluid inside the chamber 224. In some embodiments, the needle and blunt stylet are produced from stainless steel via a drawn wire process. The needle, valves, chambers, and spring housing components can be ordered to size in large volume and then assembled in clean rooms using a combination of snap-fitting and adhesive bindings, well known in the art.

In various embodiments, the needle and blunt tip are made by high temperature extrusion or (more cheaply) wire pulling of stainless steel, or some combination. In some embodiments, the spring(s) are made by wire coiling stainless steel, and the housing, valves, indicator chamber, and screwtop fixtures are made by plastic injection molding.

In some embodiments, the assembled needle is then filled with medical-grade saline or other suitable fluid and packaged sterile. Any fluid can be used as an indicator fluid, provided that the fluid does not cause injury to the patient. For example, the fluid within the chamber can be a mixture of medical-grade saline and an inert dye. Thus, in some embodiments, a non-toxic colored fluid is disposed in the pressure chamber. In some embodiments, there are some potential benefits to using a less viscous fluid that is more sensitive to pressure changes and with less adhesion to the needle walls.

This device can be used to gain entry safely into a body cavity or lumen for any purpose. Two possible applications of the technology include insufflation during laparoscopic surgery and the placement of a central line. In both of these examples, a needle is passed to the targeted position with safeguards to prevent going any further for risk of injuring the patient.

Figure 3:
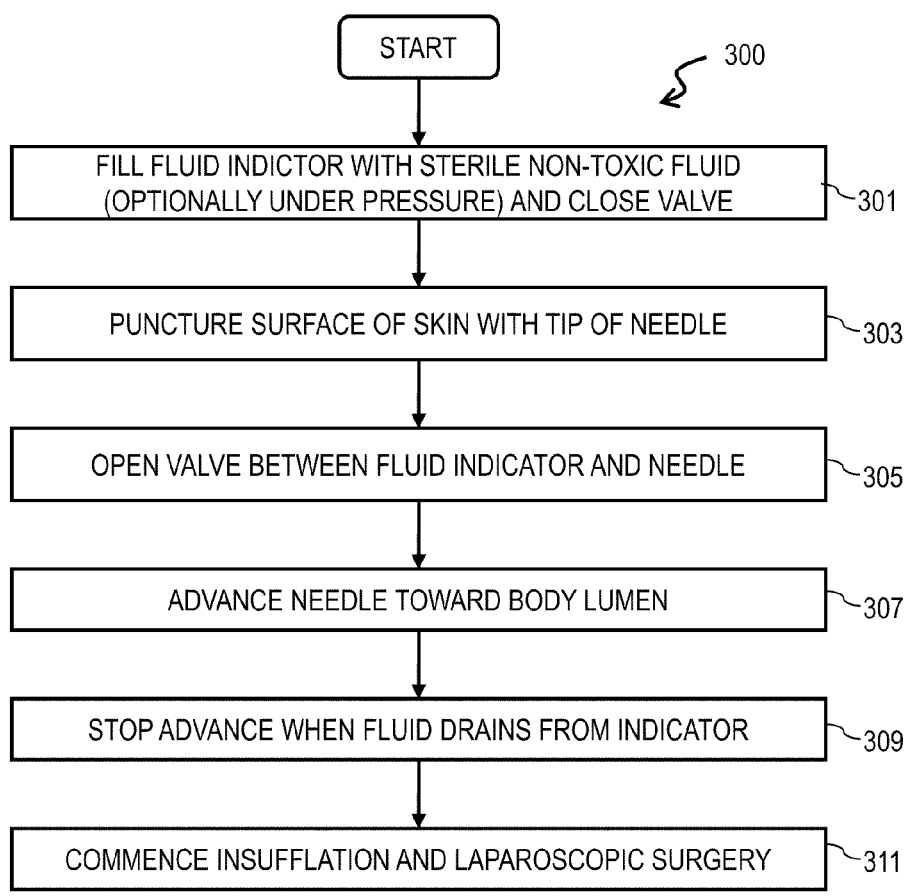
FIG. 3 is a flow chart that illustrates an example method for using the modified needle assembly for insufflation for laparoscopic surgery, according to an embodiment.

FIG. 3 is a flow chart of a method 300 for using the modified needle assembly, e.g. for insufflation for laparoscopic surgery, according to an embodiment. In step 301, the fluid chamber is filled with a non-toxic fluid, such as sterile saline, optionally under pressure; and the valve 222 is closed.

In some embodiments, the fluid is colored with a safe dye (e.g., Blueron, by FLUORON™ in Ulm, Germany) to render the fluid more visible when inside chamber 224. The medical and tissue staining properties of the dye have no necessary effect on the device's performance; the purpose of the dye is to render the fluid in the chamber 224 more visible to the surgeon. In some embodiments, the operator fills the chamber. In some embodiments, the chamber is filled by a supplier or manufacturer of the modified needle assembly 200, and step 301 is performed off site. When a distal valve 222 (or 256) is present, in some embodiments, step 301 includes closing the distal valve preventing flow of the indicator fluid when the blunt stylet is in the deployed position. In some embodiments without a distal valve, the blunt stylet is locked in a retracted position to prevent flow of the indicator fluid.

Thus step 301 includes, before puncturing the surface of the skin of the subject, disposing a quantity of non-toxic fluid into the pressure chamber 224 to a level that is a substantively constant level until entering a body lumen.

In some embodiments, step 301 also includes. before puncturing the surface of the skin of the subject and after disposing the quantity of non-toxic fluid into the pressure chamber, pressurizing the chamber 224 by attaching a pressure source to a proximal end (such as screwtop fixture 118), of the pressure chamber 224 and opening a second flow valve 116 at a proximal end of the pressure chamber 224 to increase pressure inside the pressure chamber 224. In some embodiments, pressurizing the chamber 224 further comprises closing the second flow valve 116 to maintain pressure inside the pressure chamber 224 and detaching the pressure source from the proximal end (e.g., screwtop fixture 118) of the pressure chamber 224.

Figure 4B:
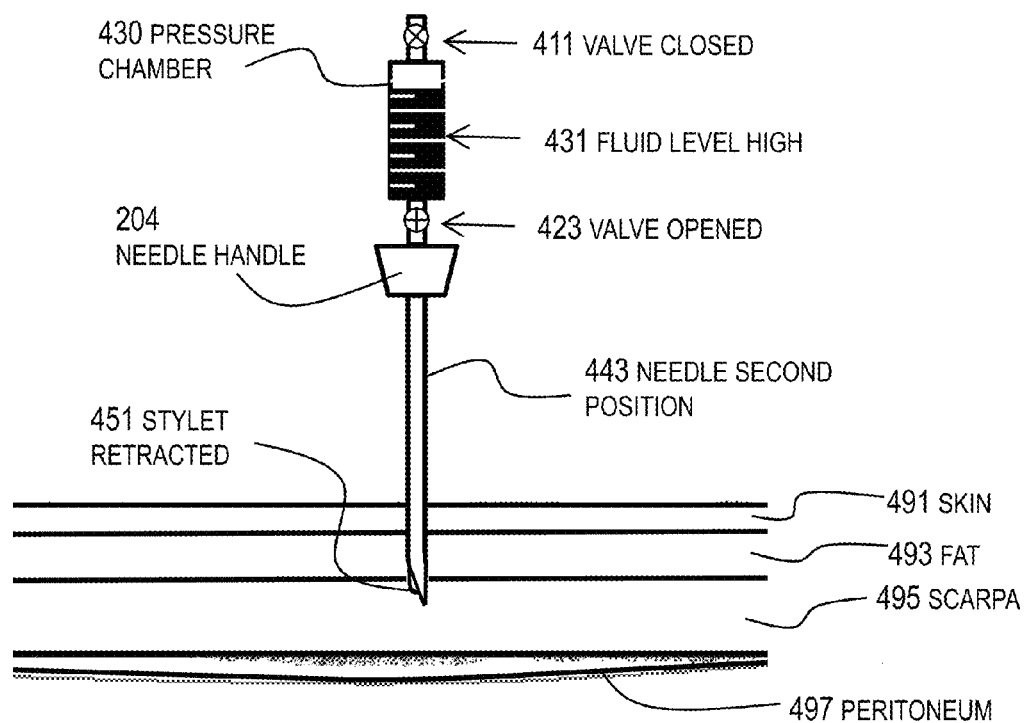
Figure 4C:
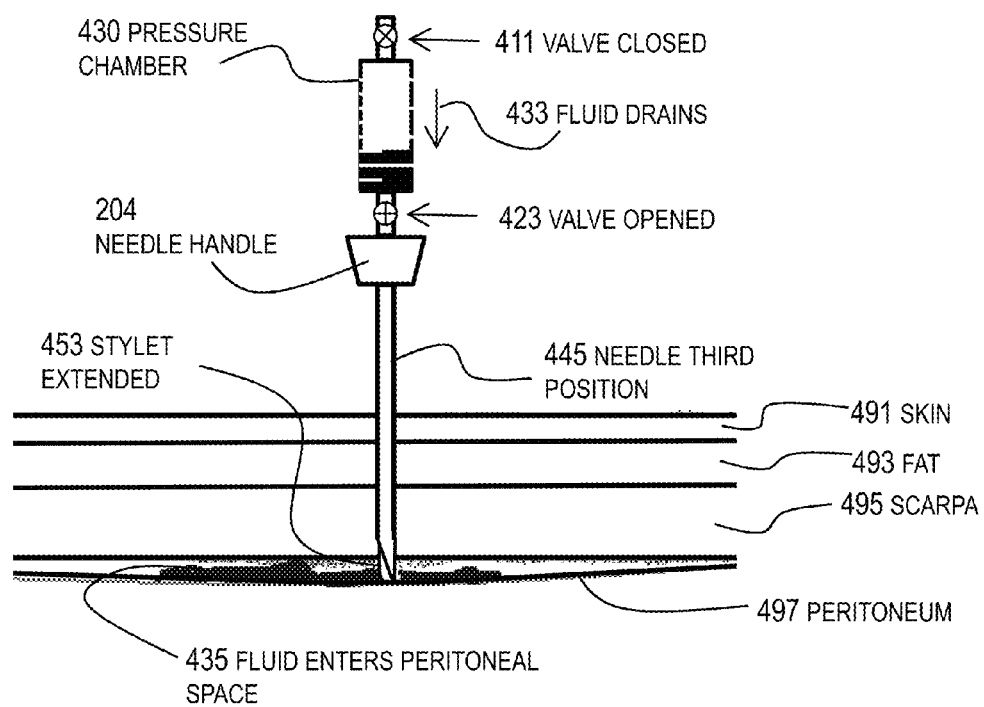

FIGS. 4A-4C are block diagrams that illustrate operation of an example modified needle assembly using the method of FIG. 3, according to an embodiment. FIG. 4A depicts the modified needle assembly 200 at the start of a procedure, before step 303. The subject is indicated by a layer of skin 491, a layer of fat 493, scarpa 495 and a peritoneum surface 497. Between the peritoneum surface 497 and scarpa 495 is the peritoneal space where the tip of the needle is to be stopped. The modified needle assembly 200 with needle handle 204 is depicted with a proximal valve 116 in closed state 411, the pressure chamber 230 pressurized with high fluid level 431, and gradation markings 432 in a contrasting color. The distal valve 222 is also in a closed state 421, and the stylet 216 is in a retracted state 451. The needle 112 is in a first position 441 outside the layer of skin 491 of the subject.

In step 303, the needle is passed through the first few layers of tissue. Thus step 303 includes puncturing a surface of skin of a subject with a sharp distal end of a hollow needle, in which a hollow stylet having a proximal end and a blunt distal end extends through the hollow needle and the blunt distal end includes an opening for passing fluid through the blunt distal end. Furthermore, an at least partially translucent pressure chamber holds a quantity of fluid under pressure and has a distal end connected through a closed flow valve to the proximal end of the stylet.

In step 305, the distal flow valve 222 is opened, allowing flow through to the interior of the blunt stylet. While the blunt tip of the stylet is still embedded in tissue, the indicator fluid is prevented from flowing and thus the fluid level in the indicator chamber remains at a fixed, reference position. In some embodiments, step 305 includes unlocking the blunt tip using the lock switch 115, allowing the pressure from tissue to keep the stylet retracted. Thus, this step includes opening the flow valve 222 after puncturing the surface of the skin of the subject.

FIG. 4B depicts the modified needle assembly 200 after step 305. The layer of skin 491, layer of fat 493, scarpa 495 and peritoneum surface 497 are as described above. The modified needle assembly 200 with needle handle 204 is depicted with the proximal valve 116 in closed state 411, the pressure chamber 430 pressurized with high fluid level 431, and gradation markings 432 in a contrasting color. The distal valve 222 is now in an opened state 423 and the stylet 216 is still in a retracted state 451 due to pressure by the tissue (e.g., scarpa 495). The needle 112 is in a second position 443 penetrating the outer layers of the subject.

In some embodiments, during step 305, the pressure and content of the indicator chamber can be optimized via the proximal fixture, e.g., female screw fixture 234a and opening proximal valve 116.

In step 307 the needle is advanced toward the body lumen, e.g., the peritoneal space. Continued progression of the needle through fascia keeps pressure on the stylet so that it remains in the retracted position, as depicted in FIG. 4B. Thus, step 307 includes, after opening the flow valve 222, advancing the distal end of the hollow needle 112 through successive fascia of tissue in the subject while the fluid is observed to remain at a substantively constant level in the pressure chamber.

In step 309, the advance of the needle is stopped when the fluid drains from the indicator. Only upon penetrating into a body lumen, such as the peritoneum, does the fluid flow due to gravity or pressure, or some combination. The fluid originally in the chamber 224 substantively drains into the lumen, which provides an instant feedback to the physician that the insertion is completed. The fluid level in the chamber does not drop quickly until the needle has entered the lumen, e.g., the peritoneal space,—thus providing a continuous and unambiguous signal of the state of penetration. Thus, step 309 involves stopping advancing the distal end of the hollow needle 112 upon observing the fluid passing out of the pressure chamber 224.

FIG. 4C depicts the modified needle assembly 200 at step 309. The layer of skin 491, layer of fat 493, scarpa 495 and peritoneum surface 497 are as described above. The modified needle assembly 200 with needle handle 204 is depicted with the proximal valve 116 in closed state 411. The needle 112 is in a third position 445 with its tip penetrating the peritoneal space. The distal valve 222 is still in an opened state 423; and, the stylet 216 has deployed to an extended state 453 due to absence of opposing tissue in the peritoneal space. Consequently, the stylet interior opening 218 is exposed to the peritoneal space and fluid flows from the pressure chamber 430 through the hollow stylet 216 and opening 218 into the peritoneal space. This action is depicted by fluid drains arrow 433 and the fluid entering the peritoneal space indicated by the dark mass 435. The pressure chamber 430 de-pressurizes, at least in part, with a low fluid level. Upon detection of this state of fluid in the pressure chamber 224, the physician stops advance of the modified needle at step 309.

In various embodiments, passage of the needle proceeds until either a body cavity (i.e. perineum or peritoneum) or lumen containing a fluid at a lower gauge pressure than that in the fluid chamber (i.e. vena cava) is reached. At such a point, the indicator fluid is no longer met with sufficient resistance and begins to rapidly evacuate from the chamber. This precipitous drop in the fluid level is easily perceptible to the physician who can then immediately stop passage of the needle in step 309. If desired, in some embodiments, the physician may move the needle through any remaining fascia with the blunt tip locked in its deployed state to prevent injury.

In step 311, an insufflation gas source is connected to screwtop fixture 118 and valve 116 is opened to begin insufflation and subsequent laparoscopy. In some embodiments, the fluid level indicator pressure chamber 230 is then removed via the distal screwtop fixture, such as female screw fixture 234b, to allow for maximal delivery of interventional or therapeutic fluids, including insufflation gases. Once entry has been achieved, the needle assembly 200 is connected to a $CO_2$ source and the cavity is expanded to create an operating space, this process is called insufflation. Subsequently, additional ports for cameras and long, surgical devices are created, usually by direct trocar insertion. The surgery may then commence. Thus step 311 includes commencing insufflation through the hollow needle 112 after stopping advancing the distal end of the hollow needle 112. For example, step 311 includes injecting gas through the hollow stylet 216 while the blunt distal end is extended through the sharp distal end of the needle 112. After insufflation, a pneumoperitoneum (e.g., a large, distended abdomen) is generated in the subject, which then makes it safe to directly insert larger ports for laprascopic instruments.

Assembly 200 does not significantly alter the standard insertion procedure, save for the operation of the flow valve 222 in step 305. Use of the modified needle assembly 200 is almost identical in function to the standard Veress needle, save for this advantgeous step. For the purposes of illustration, the needle is assumed to be pre-filled with saline and a medical-grade indicator dye for facile visualization. After initial insertion of the needle tip into the superficial fascia, valve 222 is opened. Passage through the intermediate fascia and subcutaneous layers is then continued until the target lumen is pierced, at which point the indicator pressure chamber quickly drains, signaling successful entry and passage termination. Standard $CO_2$ lines are then attached via the screwtop fixture 118 and valve 116 is opened to allow insufflation.

With the fluid level insertion indicator pressure chamber 224, the success rate of first insertion is much higher than for blind insertion. Most importantly, as a surgeon has instant feedback indicating the needle penetrating into the peritoneum, potential risks of damaging the abdominal aorta and other organs are substantively eliminated.

Additionally, the Fluid level insertion indicator has the potential to provide feedback to the surgeon if the needle has pierced an organ or a blood vessel. Any bleeding that occurs during insertion for laparoscopy forces blood up through the hollow stylet 216 into the attached chamber 224. Other than the act of actually withdrawing fluid with a syringe, few other laparoscopic devices provide feedback about whether or not the subject is bleeding.

In various other embodiments, the fluid in the indicator is changed from a colored dye in biocompatible solution to simple colorless biocompatible fluid, for example, when the surgeon is concerned with the fluid affecting his or her field of vision. Pressure in the fluid indicator is elevated in some embodiments, so that the fluid drains and fluid level inside the chamber 224 decreases even if the needle tip 210 is not below the chamber 224 in a gravitational field. A mechanical indicator of blunt tip activation is added in some embodiments to provide additional feedback to the surgeon. A lock is included in some embodiments, to prevent withdrawal of the protective blunt tip after the initial insertion, ensuring that vessels and organs beyond the peritoneal space are safeguarded.

A prototype demonstrating the feasibility of the needle and fluid chamber design was built. The device was successfully demonstrated on an approximation of the conditions of the peritoneal space. Fresh porcine parts were procured from a local butcher to simulate human tissue during a standard laparoscopic procedure. The thin, exterior lining of the stomach simulated the peritoneum, fatty porcine belly simulated human fascia, and the thin exterior casing of the small intestine was used to simulate vital viscera. The intestinal casing was pumped with air to act as an indicator of damage to vital organs, i.e. puncturing of the delicate casing would cause it to immediately deflate. The air-filled intestinal casing was placed inside of a cylindrical container. The stomach lining was extended and held taught over the entire opening of a container to simulate the peritoneum in vivo. Pork belly was placed over the taut membrane; the setup was then complete. The fluid chamber of the device was loaded with a colored fluid (Blue Gatorade). No back pressure was applied in the chamber. The needle was used to puncture the pork belly (this was done with some difficulty, although in actual practice, surgeons would use scalpels to cut the tough, exterior dura of skin). After the needle was inserted into pork belly, the lower flow valve was opened to allow the indicator to start detection of peritoneal penetration. The needle was then advanced until the indicator fluid drained from the chamber, at which time the experiment concluded.

After opening the lower flow valve, the indicator fluid did not noticeably drain while the needle was within the pork belly. This suggests that fascia itself would provide enough resistance to flow.

It was observed that once the needle punctured the peritoneum and entered the peritoneal space, the level of the indicator solution quickly falls, indicating proper penetration and positioning. Subsequently, further models of the relevant physiological surroundings were created, in which the device worked in all cases. After puncturing the stomach casing, the fluid drained steadily from the chamber. In other embodiments, the rate of flow is increased by using a small cross sectional area and/or applying back pressure in the fluid chamber. This device is thus used in some embodiments to create a $CO_2$ insufflation channel, while preventing accidental puncture of blood vessels and organs and complications arising from premature insufflations.

Furthermore, after the procedure, the intestinal casing remained inflated, indicating that it was still intact, and that the deployed stylet properly protected the delicate inner organs.

This device gives surgeons definitive, visual feedback at the exact moment of peritoneal penetration, allowing them to consistently gain access to the abdominal space without damaging vital organs or major blood vessels. This feedback comes upon peritoneal penetration, when the indicator fluid in the attached chamber immediately evacuates at a rapid rate due to the small cross-sectional area of the fluid chamber. After entry into the peritoneal space, the fluid chamber module is removed, in some embodiments, and a carbon dioxide source can be adapted to begin insufflation and laparoscopic surgery. The addition of a mechanical switch to lock in the blunt tip allows the physician to maneuver the needle without substantive danger of doing damage to the patient.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. An apparatus comprising: a handle having proximal end and distal end connected at the distal end to a hollow needle having a sharp distal end for penetrating tissue, wherein the handle and needle form a conduit for passing fluid or instruments or both through the distal end of the needle;
   a hollow stylet having a proximal end and a blunt distal end, which extends through the hollow needle, wherein the proximal end of the stylet is disposed on a proximal side of the distal end of the handle and the blunt distal end includes an opening for passing fluid through the blunt distal end;
   a spring housed within the handle for biasing the stylet to extend past the sharp distal end of the needle absent resistance by tissue against the stylet; and
   an at least partially translucent indicator chamber configured to hold visibly a quantity of indicator fluid under elevated pressure, wherein the indicator chamber has a distal end connected to the proximal end of the stylet, wherein the indicator chamber and stylet form a conduit for passing indicator fluid through the opening in the blunt distal end of the stylet when the stylet extends past the sharp distal end of the hollow needle.

2. An apparatus as recited in claim 1, wherein the stylet includes a first fixture on its proximal end and the indicator chamber includes a complementary second fixture on its distal end and the indicator chamber is removeably connected to the stylet through the first and second fixtures.

3. An apparatus as recited in claim 1, further comprising a flow valve disposed where the indicator chamber is connected to the stylet.

4. An apparatus as recited in claim 1, wherein the indicator chamber includes a first fixture on its proximal end for connection to a source of pressure.

5. An apparatus as recited in claim 4, wherein the indicator chamber includes a flow valve disposed at its proximal end, wherein the flow valve is configured for retaining pressure in the indicator chamber after removal of the source of pressure.

6. An apparatus as recited in claim 1, wherein the indicator chamber has a cross sectional length large enough to be easily viewed by a person operating the apparatus and a cross sectional width small enough so that passing a small volume of indicator fluid through the stylet makes a noticeable change in a fluid level in the indicator chamber.

7. An apparatus as recited in claim 6, wherein cross sectional length is about one centimeter and the cross sectional width is about 2 millimeters.

8. An apparatus as recited in claim 1, wherein the indicator chamber is at least partially transparent.

9. An apparatus as recited in claim 1, further comprising non-toxic colored indicator fluid disposed in the indicator chamber.

10. An apparatus as recited in claim 9, wherein: the indicator chamber further comprises gradation markings; and the colored indicator fluid is a different color from a color of the gradation markings.

11. An apparatus as recited in claim 1, wherein a float is not included in the indicator chamber.

12. A method: comprising:
   puncturing a surface of skin of a subject with a sharp distal end of a hollow needle, wherein a hollow stylet having a proximal end and a blunt distal end extends through the hollow needle and the blunt distal end includes an opening for passing fluid through the blunt distal end, and wherein an at least partially translucent indicator chamber holds visibly a quantity of indicator fluid and has a distal end connected through a closed flow valve to the proximal end of the stylet, wherein the indicator chamber and stylet form a conduit for passing indicator fluid through the opening in the blunt distal end of the stylet when the stylet extends past the sharp distal end of the hollow needle;
   opening the flow valve after puncturing the surface of the skin of the subject;
   after opening the flow valve, advancing the distal end of the hollow needle through successive fascia of tissue in the subject while the indicator fluid is observed to remain at a substantively constant level in the indicator chamber and
   stopping advancement of the distal end of the hollow needle upon observing the indicator fluid passing out of the indicator chamber;
   before puncturing the surface of the skin of the subject and after disposing the quantity of non-toxic indicator fluid into the indicator chamber, pressurizing the chamber by attaching a pressure source to a proximal end of the indicator chamber and opening a second flow valve at a proximal end of the indicator chamber to increase pressure inside the indicator chamber.

13. A method as recited in claim 12, further comprising commencing insufflation through the hollow needle after stopping advancement of the distal end of the hollow needle.

14. A method as recited in claim 13, wherein commencing insufflation through the hollow needle further comprises injecting gas through the hollow stylet while the blunt distal end is extended through the sharp distal end of the needle.

15. A method as recited in claim 13, wherein commencing insufflation through the hollow needle further comprises removing the hollow stylet through the proximal end of the hollow needle and injecting gas through the hollow needle.

16. A method as recited in claim 15, further comprising, after commencing insufflation through the hollow needle, advancing a laparoscopic instrument through the hollow needle.

17. A method as recited in claim 12, further comprising, before puncturing the surface of the skin of the subject, disposing a quantity of non-toxic indicator fluid into the indicator chamber to the substantively constant level.

18. A method as recited in claim 17, wherein: the indicator chamber further comprises gradation markings; and the non-toxic indicator fluid is a different color from a color of the gradation markings.

19. A method as recited in claim 17, wherein pressurizing the indicator chamber further comprises closing the second flow valve to maintain pressure inside the indicator chamber and detaching the pressure source from the proximal end of the indicator chamber.

* * * * *